United States Patent
Karoor et al.

(10) Patent No.: US 9,254,279 B2
(45) Date of Patent: Feb. 9, 2016

(54) NITRIC OXIDE SCAVENGERS

(75) Inventors: Sujatha Karoor, Lake Bluff, IL (US); Ton That Hai, Round Lake, IL (US); Cong Jiang, Gurnee, IL (US); Paul Sanders, Greendale, WI (US); Cliff Holmes, Glenview, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 2685 days.

(21) Appl. No.: 10/844,202

(22) Filed: May 12, 2004

(65) Prior Publication Data
US 2005/0256169 A1 Nov. 17, 2005

(51) Int. Cl.
*A61K 31/4164* (2006.01)
*A61K 31/353* (2006.01)
*A61K 31/4178* (2006.01)
*A61K 31/4439* (2006.01)

(52) U.S. Cl.
CPC ........... *A61K 31/353* (2013.01); *A61K 31/4164* (2013.01); *A61K 31/4178* (2013.01); *A61K 31/4439* (2013.01)

(58) Field of Classification Search
CPC .................................................. A63K 31/4164
See application file for complete search history.

(56) References Cited

U.S. PATENT DOCUMENTS

| 4,396,383 A | 8/1983 | Hart |
| 5,407,581 A * | 4/1995 | Onodera et al. ............. 210/654 |
| 5,431,496 A | 7/1995 | Balteau et al. |
| 5,464,857 A * | 11/1995 | Maeda et al. ................ 514/398 |
| 5,767,103 A | 6/1998 | Greenberg et al. |
| 6,319,243 B1 | 11/2001 | Becker et al. |
| 6,407,135 B1 * | 6/2002 | Lai et al. ....................... 514/423 |
| 6,623,638 B2 | 9/2003 | Watkins et al. |
| 6,663,743 B1 | 12/2003 | Becker et al. |
| 6,667,317 B2 * | 12/2003 | Chenard et al. .............. 514/323 |
| 2003/0075498 A1 | 4/2003 | Watkins et al. |
| 2003/0105424 A1 | 6/2003 | Karoor et al. |
| 2004/0026315 A1 | 2/2004 | Han et al. |

FOREIGN PATENT DOCUMENTS

WO  WO 03/084528  10/2003

OTHER PUBLICATIONS

Chiang (Mat Res Soc Symp Oric, vol. 247, 1992).*
Fricker, Expert Opinion on Investigational Drugs vol. 8, No. 8 (1999) 1209-1222.*
Jacobs et al (Replacement of Renal Function by Dialysis, 4th Ed., 1998, p. 525).*
Cirujeda et al, J. Am. Chem. Soc. 2000, 122, 11393-11405.*
James, Drugs and the pharmaceutical sciences; v 28, Mercer Dekker, New York, New York, 1986, p. 94.*
Henderson L.W., Symptomatic hypotension during hemodialysis, Kidney Int., 17, 1980 pp. 571-576.

(Continued)

*Primary Examiner* — Benjamin Packard
(74) *Attorney, Agent, or Firm* — K&L Gates LLP (57) ABSTRACT

Therapeutic compositions capable of removing excess nitric oxide are provided. The therapeutic compositions include nitronyl nitroxide monoradicals, B12 derivatives, flavonoid derivatives, the like and combinations thereof. The therapeutic compositions can be utilized in a number of suitable applications, such as to prevent or treat intradialytic hypotension during dialysis.

13 Claims, 6 Drawing Sheets

(56) References Cited

OTHER PUBLICATIONS

Henrich W.L., Hemodynamic instability during hemodialysis, Kidney Int., 30, 1986 pp. 605-612.
Converse R.L. Jr. et al., Sympathetic overactivity in patients with chronic renal failure, New Eng. J. Med., 327, 1992 pp. 1912-1918.
Malik S. et al., Chronic renal failure and cardiovascular autonome function, Nephron, 43, 1986 pp. 191-195.
Beasley D. et al., Role of nitric oxide in hemodialysis hypotension, Kidney Int., 42, 1992 pp. S96-S100 (Suppl. 38).
Shaldon S. et al., Haemodialysis hypotensia: The interleukin hypothesis restated, Proc. Eur. Dial. Transplant Assoc., 22, 1985 pp. 229-243.
Dinarello C.H., Amino acid sequences multiple biological activities and comparison with TNF, Year Immunol, 2, 1986 pp. 68-89.
Bingel H. et al., Lancet, 11, 1987 , pp. 14-16.
Lonneman G. et al., Kidney Int., 35, 1988 pp. 29-35.
Yokokawa K. et al., Ann. Int. Med. 123, 1995 pp. 35-37.
Lin S.H. et al., Asaio J., 42, 1996, pp. M895-899.
Kang E.S. et al., Am. J. Med. Sci., 313, 1997, pp. 138-143.
Martenson et al., Artif Organs, 21, 1997, pp. 163-167.
Ou J. et al., Nitric oxide Biology and Chemistry, 1(5), 1997, pp. 404-416.
Hoffman et. al, Am. J. Physiol., 272, 1997, pp. 9383-9392.
Ullman, E.F., et al., J. Amer. Chem. So., 94(2), 1972, pp. 7049.
Zhao, H.T., et al. Chinese Sci. Bull., 42(20), 1997, p. 1693.
Laude-Sharp et al., Kidney Int., 57, 1988, pp. 1084-1089.
Dodd N. et al., Inter. J. Artif. Organs, 5, 1982, pp. 272-276.
Dinarello C., Kidney Int. 41, 1992, pp. 683-694.
Tracey K. et al., Nature, 330, 1987, pp. 662-664.
Wakabayashi G. et al., FASEB J., 5, 1991, pp. 338-343.
Kilbourn, R. et al., Proc. Natl. Acad. Sci. USA, May 1990, vol. 87, pp. 3629-3632.
Kilbourn R. et al., Bio. Chem Biophy Res. Commun. 172, 1990, p. 1132.
Nunata M. et al., J. Immunol. 160, 1998, pp. 3031-3037.

\* cited by examiner

NITRIC OXIDE SCAVENGERS

BACKGROUND OF THE INVENTION

The present invention relates to therapeutic compositions. More specifically, the present invention relates to therapeutic compositions and methods of making and using same that are capable of removing excess nitric oxide effectively without inhibiting nitric oxide synthesis.

Due to disease, insult or other causes, a person's renal system can fail. In renal failure of any cause, there are several physiological derangements. The balance of water, minerals and the excretion of daily metabolic load are no longer possible in renal failure. During renal failure, toxic end products of nitrogen metabolism (e.g., urea, creatinine, uric acid, and the like) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis, hemofiltration and peritoneal dialysis are three types of dialysis therapies generally used to treat loss of kidney function. Hemodialysis treatment removes waste, toxins and excess water directly from the patient's blood. The patient is connected to a hemodialysis machine, and the patient's blood is pumped through the machine. For example, needles or catheters can be inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. A large amount of dialysate, for example about 90-120 liters, is used by most hemodialysis machines to dialyze the blood during a single hemodialysis therapy. The spent dialysate is then discarded. Hemodialysis treatment lasts several hours and is generally performed in a treatment center about three times per week.

Hemofiltration is a convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. An excessive amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution) or into the venous blood line leaving the hemofilter.

Peritoneal dialysis utilizes a sterile dialysis solution or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysate and manually infuses fresh dialysate through the catheter or other suitable access device and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient drains the spent dialysate and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysate.

In CAPD, the patient performs several drain, fill, and dwell cycles during the day, for example, about four times per day. Each treatment cycle, which includes a drain, fill and dwell, takes about four hours.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysate and to a fluid drain. The dialysis machine pumps spent dialysate from the peritoneal cavity, through the catheter, to the drain. The dialysis machine then pumps fresh dialysate from the dialysate source, through the catheter, and into the patient's peritoneal cavity. The automated machine allows the dialysate to dwell within the cavity so that the transfer of waste, toxins and excess water from the patient's bloodstream to the dialysate solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a smaller volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day.

In general, standard peritoneal dialysis solutions contain dextrose or other suitable osmotic agent at a suitable concentration, such as 1.5% to 4.25% by weight, to effect transport of water and metabolic waste products across the peritoneal membrane. Dextrose is generally recognized as a safe and effective osmotic agent, particularly for short dwell exchanges.

Although the use of dialysis and other methods for treating patients with renal disease provide treatments that allow patients with renal failure to survive, current technologies may not adequately provide a therapeutic effect necessary to address renal failure and other associated disease. For example, intradialytic hypotension (IDH) is one of the most common complications of hemodialysis. Up to one third of long term dialysis patients experience acute hypotension during hemodialysis, thus requiring premature termination of the process or requiring therapeutic intervention. See, for example, Henderson L W., Symptomatic hypotension during hemodialysis, Kidney Int. (1980) 17:571-576; Henrich W L., Hemodynamic instability during hemodialysis, Kidney Int. 1986 30:605-612; and Converse R L Jr. et al., Sympathetic overactivity in patients with chronic renal failure, New Eng J Med 1992 327:1912-1918.

The hemodialysis related hypotension is multifactorial. Failure to preserve plasma volume, pre-existence of cardiovascular disease or autonomic nervous system (ANS) dysfunction (See, for example, Malik S et al., Chronic renal failure and cardiovascular autonome function, Nephron 1986 43:191-195) can all lead to hypotension during hemodialysis, but hypotension can occur in their absence. Repetitive occurrence of these episodes can lead to diminution in both quality and span of life. For example, it has been proposed that hemodialysis associated hypotension is mediated by production of nitric oxide in vascular smooth muscle cells which may be induced by cytokines such as interleukin-1 (IL-1) or tumor necrosis factor (TNF). See, for example, Beasley D et al., Role of nitric oxide in hemodialysis hypotension, Kidney Int 1992 42:S96-S100 (Suppl. 38). Plasma levels of IL-1 and TNF are chronically elevated in patients with end stage renal disease who are undergoing dialysis. See, for example, Shaldon S et al., Haemodialysis hypotensia: The interleukin hypothesis restated. Proc Eur Dial Transplant Assoc 1985 22:229-243. This chronic elevation of plasma IL-1 and TNF may be due to decreased renal clearance (See, for example, Dinarello C H., Amino acid sequences multiple biological activities and comparison with TNF, Year Immunol 2 1986 68-89) and also increased production due to dialysis related factors. The elevated production of NO is attributed to blood monocyte activation during the interval during hemodialysis, addition of heparin, acetate-containing dialysate solution (See, for example, Bingel H et al. 1987 Lancet 11:14-16), endotoxin from dialysate (See, for example, Lonneman G et al. 1988 Kidney Int. 35:29-35), uremic platelets, and monocyte adherence to dialysis membrane.

Cytokines are powerful inducers of NOS that can result in marked elevation in NO synthesis within hours. IL-1 derived from monocytes and macrophages was postulated to account for overproduction of NO (macrophage dependent). Several studies (See, for example, Yokokawa K et al., 1995 Ann Int Med 123 35-37; Lin S H et al., 1996 ASAIO J 42:M895-899; Kang E S et al., 1997 Am J Med Sci 313:138-143; and Martenson et al., 1997 Artif Organs 21:163-167), have also shown that NO overproduction is associated with hypotension during hemodialysis. Several aspects of hemodialysis procedure activate macrophages to produce NO that initiates a cycle/cascade of inflammatory response resulting in NO overproduction that leads to hypotension. In addition to playing a key role in the inflammatory cycle, NO plays a major role in blood pressure regulation. NOS inhibitors are not very specific and tend to shut down iNOS as well as other NOS isoforms that regulate normal physiology. iNOS has been shown to have homeostasis functions, protecting against liver damage by inhibiting apoptosis (See, for example, Ou J et al., 1997 Nitric oxide Biology and Chemistry 1(5) 404-416) and maintaining musosal barrier function in the gut (Hoffman et al, 1997 Am J Physiol 272 9383-9392).

A need therefore exists to provide improved compositions that can be utilized to effectively remove nitric oxide from plasma and/or at the cellular level to protect against disease, such as intradialytic hypotension.

SUMMARY OF THE INVENTION

The present invention relates to therapeutic compositions and methods of making and using same. In particular, the present invention relates to nitric oxide scavenger compositions that are capable of removing excess nitric oxide while preserving a sufficient amount of nitric oxide necessary for homestasis effectively without inhibiting nitric oxide synthesis.

To this end, in an embodiment, the present invention provides a composition capable of removing excess nitric oxide that can be utilized in a number of different applications, such as dialysis. The composition includes a pharmaceutically active agent including a nitronyl nitroxide monoradical, a B12 derivative, a flavonoid derivative, derivatives thereof, the like and combinations thereof In an embodiment, the nitronyl nitroxide monoradical includes:
   1,3-dihydroxy-2-(2,4-dihydroxyphenyl)-4,4,5,5-tetramethylimidazolidine;
   1,3-dihydroxy-2-(3,4-dihydroxyphenyl)-4,4,5,5-tetramethylimidazolidine;
   1,3-dihydroxy-2-(4-pyridyl)-4,4,5,5-tetramethylimidazolidine;
   1,3-dihydroxy-2-(2-thienyl)-4,4,5,5-tetramethylimidazolidine; 1,3-Dihydroxy-2-(2-furyl)-4,4,5,5-tetramethylimidazolidine; the like; and
   combinations thereof.

In an embodiment, the B12 derivative includes hydroxocobalamin, cyanocobalamin, the like and combinations thereof.

In an embodiment, the flavonoid derivative includes pelargonidin, cyanidin, delphinidin, the like and combinations thereof.

In another embodiment, a semipermeable membrane for performing dialysis is provided. The semipermeable membrane includes a membrane material that has a modified surface such that the membrane is capable of removing excess nitric oxide from a fluid undergoing dialysis.

In an embodiment, the modified surface includes a ligand attached thereto allowing the semipermeable membrane to remove excess nitric oxide.

In an embodiment, the ligand includes a derivatized compound including a nitronyl nitroxide monoradical, a B12 derivative, a flavonoid derivative, the like and combinations thereof.

In an embodiment, the derivatized compound includes:
   1,3-dihydroxy-2-(2,4-dihydroxyphenyl)-4,4,5,5-tetramethylimidazolidine;
   1,3-dihydroxy-2-(3,4-dihydroxyphenyl)-4,4,5,5-tetramethylimidazolidine;
   1,3-dihydroxy-2-(4-pyridyl)-4,4,5,5-tetramethylimidazolidine;
   1,3-dihydroxy-2-(2-thienyl)-4,4,5,5-tetramethylimidazolidine; 1,3-Dihydroxy-2-(2-furyl)-4,4,5,5-tetramethylimidazolidine;
   hydroxocobalamin; cyanocobalamin; pelargonidin; cyanidin; delphinidin; the like and combinations thereof.

In an embodiment, the membrane material includes a polysulfone, cellulose, cellulose acetate, polyamide, polyacrylonitrile, polyvinylalcohol, polymethyl methacrylate, polyolefin, the like and combinations thereof.

In yet another embodiment, a pharmaceutical agent in solution form is provided. The pharmaceutical agent includes a compound, such as a nitronyl nitroxide monoradical, a B12 derivative, a flavonoid derivative, the like and combinations thereof wherein the pharmaceutical agent is capable of removing an excess amount of nitric oxide at a cellular level effectively without inhibiting nitric oxide synthesis.

In still yet another embodiment, a device for use in a dialysis system is provided. The device includes a material including a pharmaceutically active compound. The compound includes, for example, nitronyl nitroxide monoradical, a B12 derivative, a flavonoid derivative and combinations thereof wherein the pharmaceutically active compound is capable of removing an excess amount of nitric oxide from a fluid as the fluid passes through the device.

In an embodiment, the device includes a dialyzer that includes a semipermeable membrane having the pharmaceutically active compound attached thereto.

In an embodiment, the semipermeable membrane includes a polysulfone, cellulose, cellulose acetate, polyamide, polyacrylonitrile, polyvinylalcohol, polymethyl methacrylate, polyolefin, the like and combinations thereof.

In an embodiment, the device includes a cartridge. The cartridge includes a body having an inlet end and an outlet end and an interior wherein the material is contained within the interior such that the interior is so constructed and arranged that the fluid entering the inlet end flows through the material.

In an embodiment, the material includes a resin material that has the pharmaceutically active compound attached thereto.

In an embodiment, the material includes a bead material that has the pharmaceutically active compound attached thereto.

In an embodiment, the material includes a membrane material that has the pharmaceutically active compound attached thereto.

In a further embodiment, a method of providing dialysis to a patient is provided. The method includes providing a composition including a pharmaceutically active agent wherein the pharmaceutically active agent includes a nitric oxide scavenger composition; providing the composition to the patient; and removing an excess amount of nitric oxide from the patient without inhibiting synthesis of nitric oxide.

In an embodiment, the composition is administered intravenously to the patient.

In an embodiment, the composition is orally administered to the patient.

In an embodiment, the pharmaceutically active agent is attached to a semipermeable membrane material within a dialyzer allowing removal of the excess amount of nitric oxide during dialysis.

In an embodiment, the pharmaceutically active agent is attached to a bead material within a cartridge further allowing removal of the excess amount of nitric oxide during dialysis.

In yet a further embodiment, a method of preventing or treating intradialytic hypotension in a patient undergoing dialysis is provided. The method includes providing a composition to the patient wherein the composition includes a pharmaceutically active agent that includes a nitric oxide scavenger composition; and removing an excess amount of nitric oxide from the patient without inhibiting synthesis of nitric oxide.

In still yet a further embodiment, the present invention provides a dialysis solution. The dialysis solution includes a nitronyl nitroxide manoradical, a B12 derivative, a flavonoid, the like and combinations thereof.

In an embodiment, the dialysis solution includes a peritoneal dialysis solution.

In an embodiment, the peritoneal dialysis solution includes a number of solution parts.

An advantage of the present invention is to provide improved therapeutic compositions.

Another advantage of the present invention is to provide improved methods of making and using therapeutic compositions that are capable of removing excess nitric oxide from plasma and/or at the cellular level without inhibiting nitric oxide synthesis.

Yet another advantage of the present invention is to provide improved dialysis solutions that include therapeutic compositions capable of removing excess nitric oxide.

Still yet another advantage of the present invention is to provide improved membranes for dialysis that are capable of removing an excess amount of nitric oxide in the dialysis fluid undergoing dialysis.

A further advantage of the present invention is to provide improved methods of performing dialysis that include administering therapeutic compositions that can be used to prevent and/or treat intradialytic hypotension and the like.

A still further advantage of the present invention is to inhibit the activity of excess nitric oxide in plasma, at the cellular level and the like.

Another advantage of the present invention is to reduce inflammation and oxidative stress in kidney disease patients.

Additional features and advantages of the present invention are described in, and will be apparent from, the following Detailed Description of the Invention and the figures.

DETAILED DESCRIPTION OF THE INVENTION

The present invention relates to therapeutic compositions and methods of making and using same. More specifically, the present invention relates to nitric oxide scavenger compositions that are capable of removing excess nitric oxide while preserving a sufficient amount of nitric oxide necessary for homestasis effectively without inhibiting nitric oxide synthesis. The present invention can be applied in numerous types of suitable applications, particularly suited for dialysis therapy.

It should be appreciated that the present invention can be used in a variety of different and suitable dialysis therapies to treat kidney failure. Dialysis therapy as the term or like terms are used throughout the text is meant to include and encompass any and all suitable forms of therapies that utilize the patient's blood to remove waste, toxins and excess water from the patient. Such therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. In an embodiment, the dialysis solutions are used during peritoneal dialysis, such as automated peritoneal dialysis, continuous ambulatory peritoneal dialysis, continuous flow peritoneal dialysis and the like. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis, peritoneal dialysis and hemodiafiltration) may be used in the in center, self/limited care as well as the home settings.

As previously discussed, the present invention relates to therapeutic compositions that are capable of removing excess nitric oxide from plasma, at the cellular level and/or the like. This can effectively prevent or treat intradialytic hypotension and/or other associated disease that can be problematic during dialysis therapy. The compositions of the present invention can include any variety of types of compositions and amounts thereof and can be used in a number of different and suitable types of applications.

In an embodiment, the composition includes, a nitronyl nitroxide monoradical, a B12 derivative, a flavonoid derivative, the like and combinations thereof.

The nitronyl nitroxide monoradical in an embodiment includes:
1,3-dihydroxy-2-(2,4-dihydroxyphenyl)-4,4,5,5-tetramethylimidazolidine;
1,3-dihydroxy-2-(3,4-dihydroxyphenyl)-4,4,5,5-tetramethylimidazolidine;
1,3-dihydroxy-2-(4-pyridyl)-4,4,5,5-tetramethylimidazolidine;
1,3-dihydroxy-2-(2-thienyl)-4,4,5,5-tetramethylimidazolidine; 1,3-Dihydroxy-2-(2-furyl)-4,4,5,5-tetramethylimidazolidine;
the B12 derivative includes hydroxocobalamin, cyanocobalamin; and the flavonoid derivative includes pelargonidin, cyanidin, delphinidin, and the like.

The therapeutic compositions of the present invention can include any suitable form. Preferably, the compositions are formed as a solid, such as a crystalline solid, an amorphous solid and the like as described below in greater detail. The compositions can then be added to a solvent, such as water, in any suitable amount to form a solution. In solution form, the therapeutic compositions can be utilized for therapy purposes in any suitable manner. Preferably, the therapeutic compositions of the present invention are utilized during dialysis therapy to prevent and/or treat intradialytic hypotension and other associated disease. The ability of the compositions to act as nitric oxide scavengers allows them to remove excess nitric oxide in plasma, at the cellular level and/or the like during dialysis therapy effectively without inhibiting nitric oxide synthesis.

Examples of compositions illustrative of the present invention are provided below pursuant to an embodiment without limitation thereof.

Synthesis of Nitronyl Nitroxide Monoradicals

Figure 1:
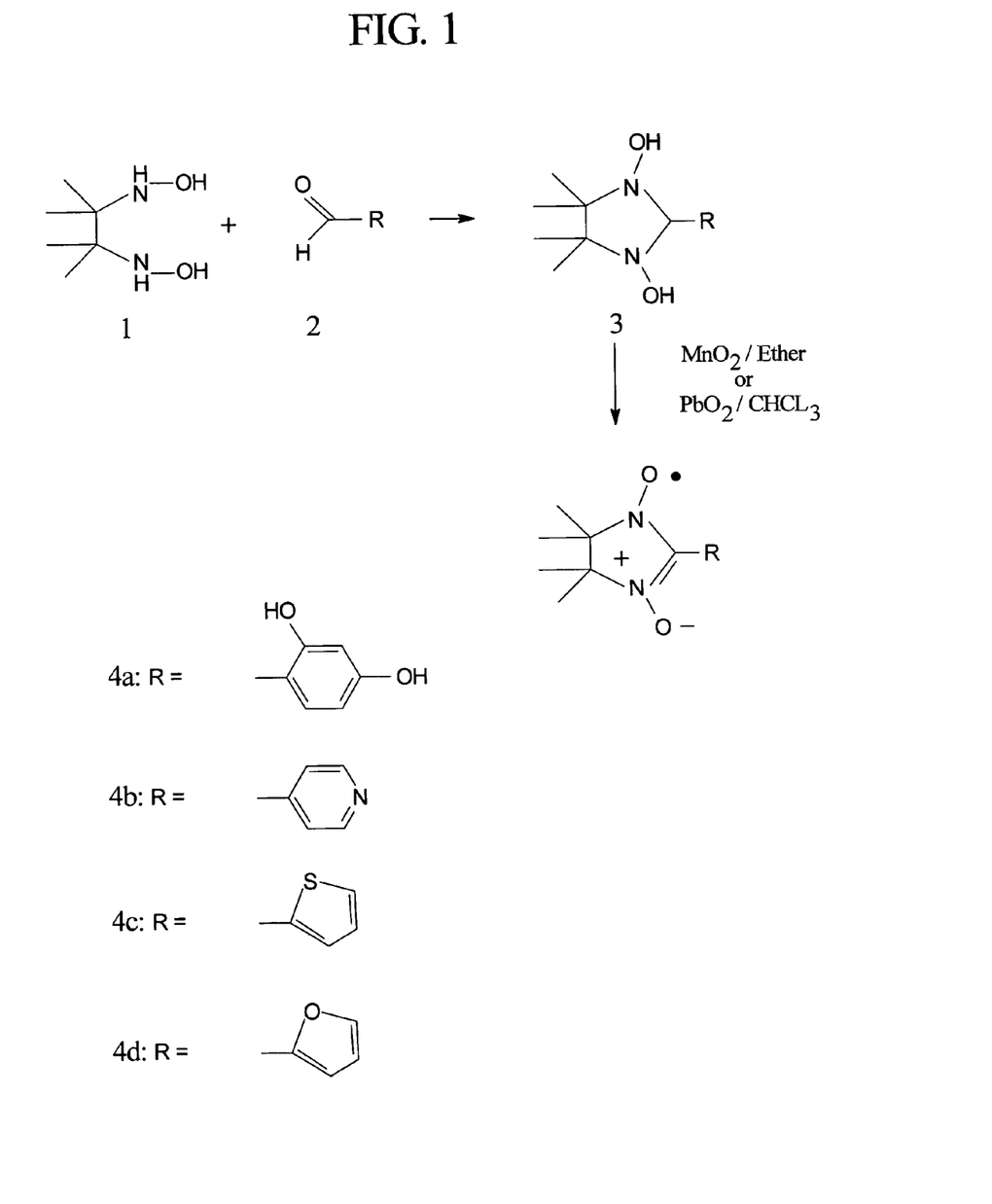
FIG. 1 schematically illustrates the synthesis of nitronyl nitroxide monoradicals according to various embodiments of the present invention.

Three nitronyl nitroxide monoradicals represented by compounds 4a, 4b and 4c have been synthesized as illustrated in FIG. 1 and as described in greater detail below. Synthesis of some of the intermediates was completed by the reported methods. See, for example, Ullman, E. F.; Osiecki, J. H.; Boocock, D. G. B. and Darcy, R.; J. Amer. Chem. So., 1972, 94(2), 7049; Maeda, H. et. al.; U.S. Pat. No. 5,464,857, 1995; and Zhao, H. T.; Liu, L.; Zhang, J. Z.; Cong, J. B.; Wu, K. and Sun, C. P.; Chinese Sci. Bull., 1997, 42(20), 1693. The nitric oxide scavenging properties of the above-referenced compounds made pursuant to various embodiments of the present invention have been investigated and reported as described below.

Synthesis of 1,3-Dihydroxy-2-(2,4-dihydroxyphenyl)-4,4,5,5-tetramethylimidazolidine (compound 4 where R is compound 4a, FIG. 1): 2,3-bis-(hydroxyamino)-2,3-dimetylbutansulfate (compound 1, FIG. 1) (2.83 g) was suspended in water (10 ml) and saturated $NaHCO_3$ was used to neutralize the mixture to pH 7.5. 2,4-dihydroxybenzaldehyde (compound 2, where R is compound 4a, FIG. 1) (1.4 g) was dissolved in methanol (100 ml) and was added to the mixture. The mixture was stirred at room temperature overnight and TLC show a formation of a new product 3, where R is compound 4a (FIG. 1), with low $R_f$. The mixture was filtered to remove the sodium sulfate and the solvent was evaporated to dryness. The residue was a mixture of compounds 2 and 3, as discussed above. This mixture (200 mg) was suspended in ether (20 ml) and 2.0 g of manganese oxide was added. The mixture was stirred at room temperature overnight and a dark blue solution was formed. TLC showed a new product as a blue band on TLC plate. The mixture was filtered and the filtrate was evaporated to dryness. The residue was passed a silica gel column to get blue color product 4 (2.5 mg) where R is compound 4a (FIG. 1).

Synthesis of 1,3-Dihydroxy-2-(4-pyridyl)-4,4,5,5,-tetramethylimidazolidine (compound 4 where R is compound 4b, FIG. 1): 2,3-bis-(hydroxyamino)-2,3-dimetylbutansulfate represented by compound 1 (FIG. 1) (5.66 g) was suspended in 20 ml of water and saturated $NaHCO_3$ was used to neutralize the mixture to pH 7.5. 4-pyridine-carboxaldehyde as represented by compound 2 (2.2 g) where R is compound 4b (FIG. 1) was added to the mixture. The mixture was stirred at room temperature for 6 hours and the white precipitate was collected through filtration. The solid was washed by ether (10 ml) and was dried under high vacuum overnight to provide white solid (2.0 g) as product 3, where R is compound 4b (FIG. 1), as characterized by NMR as follows: 1) $^1$H-NMR (DMSO-d6), 1.04(s, 6H), 1.09(s, 6H), 4.53(s, 1H), 7.48(d, 2H), 7.95(s, 2H), 8.53(dd, 2H); and 2) $^{13}$C-NMR (DMSO-$d_6$), 18.60, 25.56, 67.83, 90.45, 124.76, 150.42, 152.01.

Compound 3 (2.0 g), where R is compound 4b, was suspended in chloroform (300 ml) and lead oxide (30 g) was added. The mixture was stirred at room temperature for 1 hour and a dark blue solution was formed. TLC showed a new product as a blue band on TLC plate. The mixture was filtered and the filtrate was evaporated to dryness. The residue was crystallized from ether-hexane to give a blue crystal as product 4 (1.67 g), where R is compound 4b, that had a melting point (mp) of 144° C.-145° C.

Synthesis of 1,3-Dihydroxy-2-(2-thienyl)-4,4,5,5,-tetramethylimidazolidine (compound 4 where R is 4c, FIG. 1): 2,3-bis-(hydroxyamino)-2,3-dimetylbutansulfate (compound 1, FIG. 1) (1.5 g) was suspended in water (10 ml) and saturated $NaHCO_3$ was used to neutralize the mixture to pH 7.5. 2-Thiophenecarboxaldehyde (compound 2 where R is compound 4c, FIG. 1) (1.0 g) was dissolved in methanol (30 ml) and was added to the mixture. The mixture was stirred at room temperature overnight and TLC show a formation of a new product 3 where R is compound 4c (FIG. 1) with lower $R_f$. The mixture was filtered to remove the sodium sulfate and the solvent was evaporated to dryness. The residue (1.0 g) was a mixture of compounds 2 and 3 where R is compound 4c (FIG. 1). This mixture (200 mg) was passed a silica gel column to get of pure compound 3 (50 mg) where R is compound 4c (FIG. 1) as characterized by NMR as follows: 1) $^1$H-NMR (DMSO-d6), 1.06(s, 6H), 1.08(s, 6H), 4.78(s, 1H), 6.97(dd, 1H), 7.08(d, 1H), 7.41(d, 1H), 7.95(s, 2H); and 2) $^{13}$C-NMR (DMSO-d6), 17.98, 25.09, 67.15, 87.56, 125.91, 126.57, 127.05, 148.05. This mixture (0.8 g) was suspended in chloroform (100 ml) and lead oxide (20 g) was added. The mixture was filtered and the filtrate was evaporated to dryness. The residue was passed through a silica gel column and a blue crystal (186 mg) (compound 4 where R is compound 4c, FIG. 1) was obtained after crystallization from ether-hexane and displayed a melting point of 102° C.-104° C.

Applicants conducted a number of experiments that demonstrate the beneficial effects of the present invention as provided below without limitation.

Synthesis Procedures

Three nitronyl nitroxide monoradicals (compound 4 where R is compound 4a, 4b or 4c) have been synthesized as described above and below and further illustrated in FIG. 1 according to reported methods. See, for example, Ullman, E. F.; Osiecki, J. H.; Boocock, D. G. B. and Darcy, R.; J. Amer. Chem. So., 1972, 94(2), 7049; Maeda, H. et. al.; U.S. Pat. No. 5,464,857, 1995,; and Zhao, H. T.; Liu, L.; Zhang, J. Z.; Cong, J. B.; Wu, K. and Sun, C. P.; Chinese Sci. Bull., 1997, 42(20), 1693.

Synthesis of 1,3-Dihydroxy-2-(2,4-dihydroxyphenyl)-4,4,5,5,-tetramethylimidazolidine (compound 4 where R is compound 4a) was conducted as shown in FIG. 1. Anhydro adduct compound 3 where R is compound 4a was synthesized from treatment of 2,3-bis-(hydroxyamino)-2,3-dimetylbutansulfate (compound 1 where R is compound 4a) and 2,4-dihydroxybenzaldehyde (compound 2 where R is compound 4a) in a mixture of water and methanol. The nitronyl nitroxide monoradical (compound 4 where R is compound 4a) was obtained after oxidation of compound 3 (where R is compound 4a) with manganese dioxide in ether. Compound 4 was very unstable where only 2.5 mg of compound 4 was obtained after column chromatography.

Synthesis of 1,3-dihydroxy-2-(4-pyridyl)-4,4,5,5,-tetramethylimidazolidine compound 4 where R is compound 4b was conducted as illustrated in FIG. 1. Anhydro adduct (compound 3, where R is 4b) was synthesized from treatment of 2,3-bis-(hydroxyamino)-2,3-dimetylbutansulfate (compound 1 where R is compound 4b) and 4-pyridine-carboxaldehyde (compound 2 where R is compound 4b) in water where compound 3 was a stable white solid insoluble in water. Compound 3 was oxidized by lead oxide in chloroform to form blue crystals (compound 4 where R is compound 4b).

Synthesis of 1,3-dihydroxy-2-(2-thienyl)-4,4,5,5,-tetramethylimidazolidine (compound 4 where R is compound 4c) was conducted as shown on FIG. 1. Anhydro adduct (compound 3 where R is compound 4c) was synthesized from treatment of 2,3-bis-(hydroxyamino)-2,3-dimetylbutansulfate (compound 1 where R is compound 4c) and 2-thiophenecarboxaldehyde (compound 2 where R is compound 4c) in water and methanol where compound 3 was a stable white solid insoluble in water. Compound 3 was oxidized by lead oxide in chloroform to form blue crystals (compound 4 where R is 4c). The nitronyl nitroxide monoradicals (compound 4 where R is compound 4a, 4b or 4c) were soluble in phosphate buffer. The nitronyl nitroxide monoradicals (compound 4 where R is compound 4a or 4b) have been tested for nitric oxide scavenge activity as described below in greater detail.

NO Scavenger Assessment

The nitric oxide (NO) scavenging activity of various compounds was determined by the direct measurement of nitric oxide. Using a NO-selective microelectrode (World Precision Instruments, ISO-NO Mark II) the nitric oxide concentration was monitored upon the addition of the test compound. The reaction rate constant was calculated for each compound. Test compounds were added in molar excess, and therefore pseudo first-order reaction kinetics were observed. The rate constant (ln $k_s$) for each compound was calculated. Reactions were performed under anaerobic conditions at room temperature, in phosphate buffer (50 mM, pH 7.4). The results are shown below in Table I:

TABLE I

| | Rate of NO Scavenging | | | | | | | | | | | | | | | | | |
|---|---|---|---|---|---|---|---|---|---|---|---|---|---|---|---|---|---|---|
| Molar Ratio Scavenger | Vitamin B$_{12a\,(acetate)}$ | | | | NN-2 | | | Carboxy-PTIO | | | | Pelargonidin | | | | NN-3 | | |
| to NO | 33:1 | 47:1 | 142:1 | 277:1 | 25:1 | 42:1 | 111:1 | 28:1 | 56:1 | 91:1 | 129:1 | 40:1 | 66:1 | 370:1 | 871:1 | 25:1 | 71:1 | 126:1 |
| ln $k_s$ | 3.7 | 3.4 | 3.7 | 3.1 | 3.9 | 3.7 | 3.4 | 3.8 | 3.9 | 3.5 | 3.4 | 1.5 | 1.7 | 2.0 | 2.5 | 2.8 | 2.8 | 2.8 |

The nitric oxide scavenge activity has been determined for a number of different classes of compounds as shown above in Table I. NN-2 represents compound 4 where R is compound 4b; and NN-3 represents compound 4 where R is compound 4c as illustrated in FIG. 1. The results indicate, for example, that the nitronyl nitroxide monoradical (NN-2) has nitric oxide scavenge activity similar to that of vitamin B12a.

Hydroxocobalamin Animal Study

Applicants have conducted a study to assess the effect of hydroxocobalamin on the mean arterial pressure (MAP) and heart rate (HR) of anesthetized rats that had been treated with LPS to induce hypotension as described in greater detail below.

Three male Sprague-Dawley rats were acutely instrumented with femoral arterial and venous catheters. Rats were initially anesthetized using a 60 mg/kg i.p. dose of Nembutal (sodium pentobarbital.) Each rat was then instrumented with one arterial catheter for blood pressure measurement, and two venous catheters for test article administration, and infusion of Nembutal (0.42 mL/kg/hr) for maintenance of surgical anesthesia. After placement of the catheters, rats were moved to plexiglass boxes to begin hemodynamic measurements. Baseline data were collected for 30 minutes prior to experimental manipulation in order to verify that all rats were properly anesthetized, and that baseline MAP and HR were within acceptable baseline ranges. Following baseline data collection, each rat received a 5 mg/kg intravenous dose of LPS at a rate of 1 mL/min. After achieving a sustained hypotension at approximately 60 minutes after the LPS infusion, one rat received a 6 mL/kg intravenous dose of hydroxocobalamin (14.5 mM in PBS) over a period of one hour. The remaining two rats each received a 4.57 mL/kg intravenous dose of saline over a period of one hour. MAP and HR measurements continued for 2 hours after hydroxocobalamin or saline infusion. Following LPS administration, all three rats received a continuous intravenous administration of Lactated Ringer's solution in order to prevent dehydration (2.4 mL/kg/hr). Due to a limited amount of hydroxocobalamin, it was only possible to dose one animal with this compound.

Figure 2:
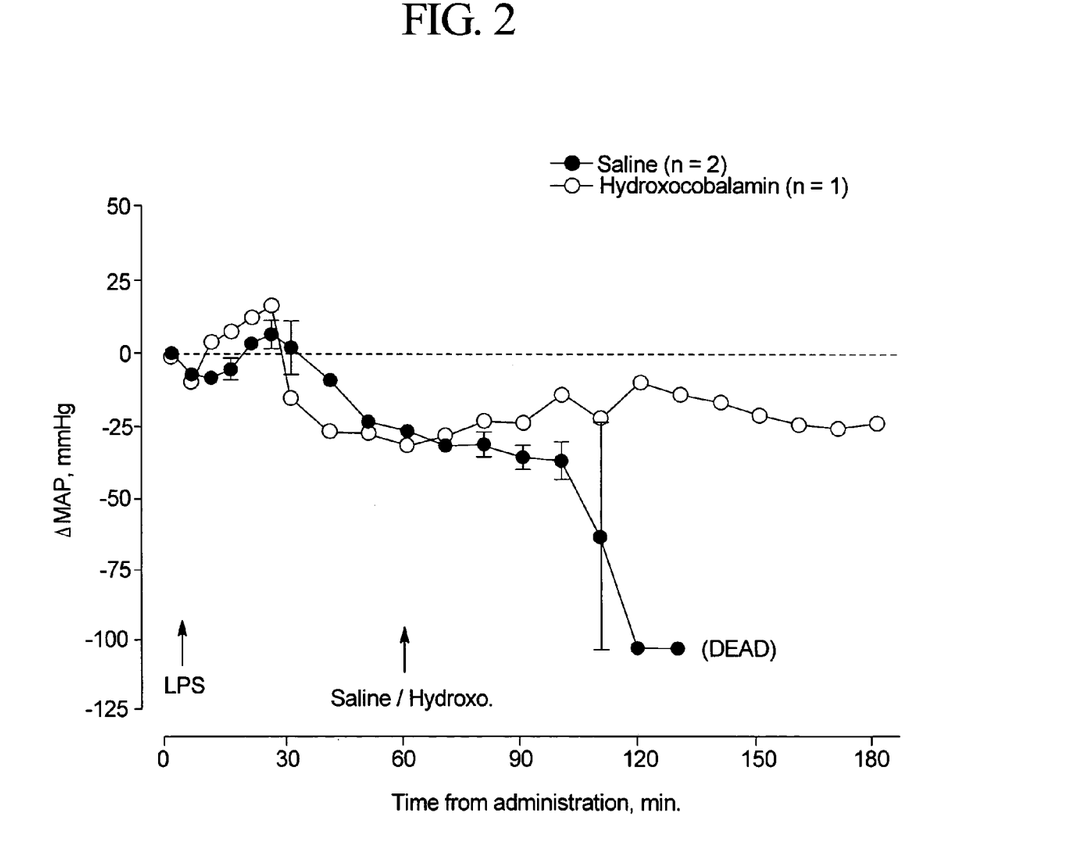
FIG. 2 graphically illustrates a mean arterial pressure response pursuant to a test conducted according to an embodiment of the present invention.

Following administration of LPS, MAP increased approximately 15-20 mmHg for 30 minutes after which MAP decreased to approximately 25-30 mmHg below baseline levels (FIG. 2). One rat received hydroxocobalamin at 60 minutes post-LPS infusion (open circles, FIG. 2). From 60-180 minutes post-LPS, MAP increased slightly to approximately 10-20 mmHg below baseline levels in this rat. This rat survived the entire experiment. The remaining two rats each received saline at 60 minutes post-LPS infusion (dark symbols, FIG. 2). From 60-100 minutes post-LPS, MAP continued to decline, and both rats died at approximately 120 minutes post-LPS.

Figure 3:
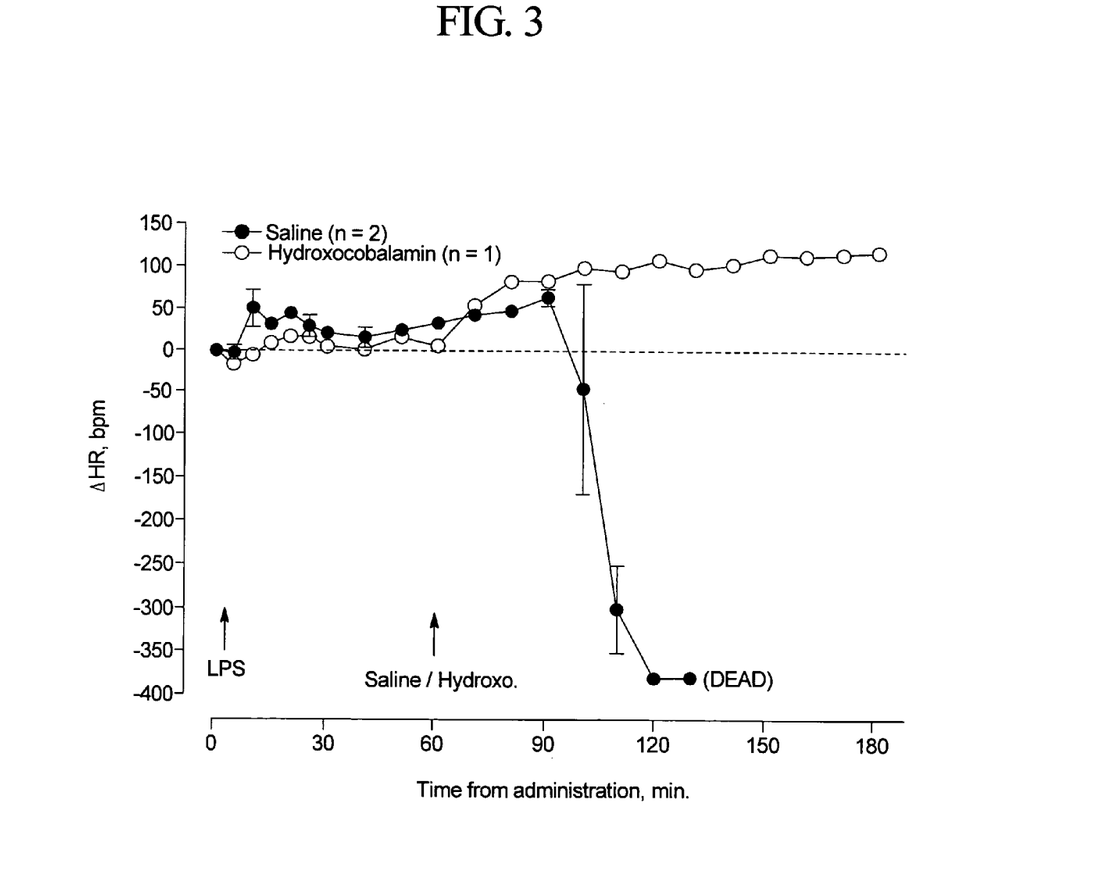
FIG. 3 graphically illustrates a heart rate response pursuant to a test conducted according to an embodiment of the present invention.

Following administration of LPS, HR increased in all animals by approximately 25 bpm (FIG. 3). At 60 minutes post-LPS infusion, HR in the rat received hydroxocobalamin increased to approximately 140 bpm above baseline levels (open circles, FIG. 3). HR in the two rats that received saline increased until approximately 90 minutes post-LPS when it began to decline (dark symbols, FIG. 3). These rats both died at approximately 110 minutes post-LPS.

The results of the above-described experiments in anesthetized rats demonstrate that LPS administration caused marked hypotension. Hydroxocobalamin administration increased HR and allowed MAP to be maintained. In contrast, the two rats that received saline after LPS were unable to maintain MAP or HR and died approximately 90 minutes after saline administration.

As previously discussed, the present invention includes membranes with excess nitric oxide removing properties according to an embodiment. The membranes include, in an embodiment, a membrane material that has one or more ligands attached thereto. The ligands are composed of the therapeutic compositions, such as the nitronyl nitroxide monoradicals, the B12 derivatives, the flavonoid derivatives, the like and combinations thereof as previously discussed.

The membranes can be made in any suitable manner. The ligands can be synthesized according to procedures as discussed above pursuant to various embodiments of the present invention. The membrane material surface is modified in any suitable manner. Once modified, the ligand or ligands can be attached to the modified surface through immobilization and/or other suitable techniques. Various factors that can effect immobilization include, for example, pH, buffer, ionic strength, and ligand concentration.

The membranes can be utilized in a number of different and suitable applications. For example, the membranes can include semipermeable membranes that can be utilized during dialysis applications. The semipermeable membranes can include a variety of suitable types, such as semipermeable polysulfone membranes. Examples of polysulfone membranes according to an embodiment of present invention can be found in U.S. patent application Ser. No. 10/327,564, entitled MELT-SPUN POLYSULFONE SEMIPERMEABLE MEMBRANES AND METHOD FOR MAKING THE SAME, filed on Dec. 20, 2002, the disclosure of which is herein incorporated by reference. It should be appreciated that the membrane can be made from any suitable type, amount and combination of materials. Additional other types of membrane compounds include cellulose, cellulose acetate, polyamide, polyacrylonitrile, polyvinylalcohol, polymethyl methacrylate, polyolefin, the like and combinations thereof. The membranes can be made with any suitable other type of ingredients, such as solvents, non-solvents, the like and combinations thereof. The membranes can be made in any suitable manner, such as solution-spinning, melt-spinning, the like and combinations thereof.

As previously discussed, the present invention includes devices that are capable of removing excess nitric oxide from a fluid, such as a fluid undergoing dialysis. The device can include any number and suitable different devices, such as a dialyzer, a cartridge or column and/or the like that can be utilized during dialysis therapy. In general, the device contains the therapeutic compositions of the present invention in any suitable way. In contact with the fluid, the compositions can effectively act to remove excess nitric oxide from the fluid as it undergoes dialysis or other suitable form of medical therapy. It should be appreciated that the device can be configured and arranged in any suitable manner such that the therapeutic material can be effectively utilized to remove excess nitric oxide. For example, the therapeutic compositions of the present invention can be attached to a membrane within a dialyzer, a bead material or the like within a cartridge and/or the like to remove excess levels of nitric oxide.

Figure 4:
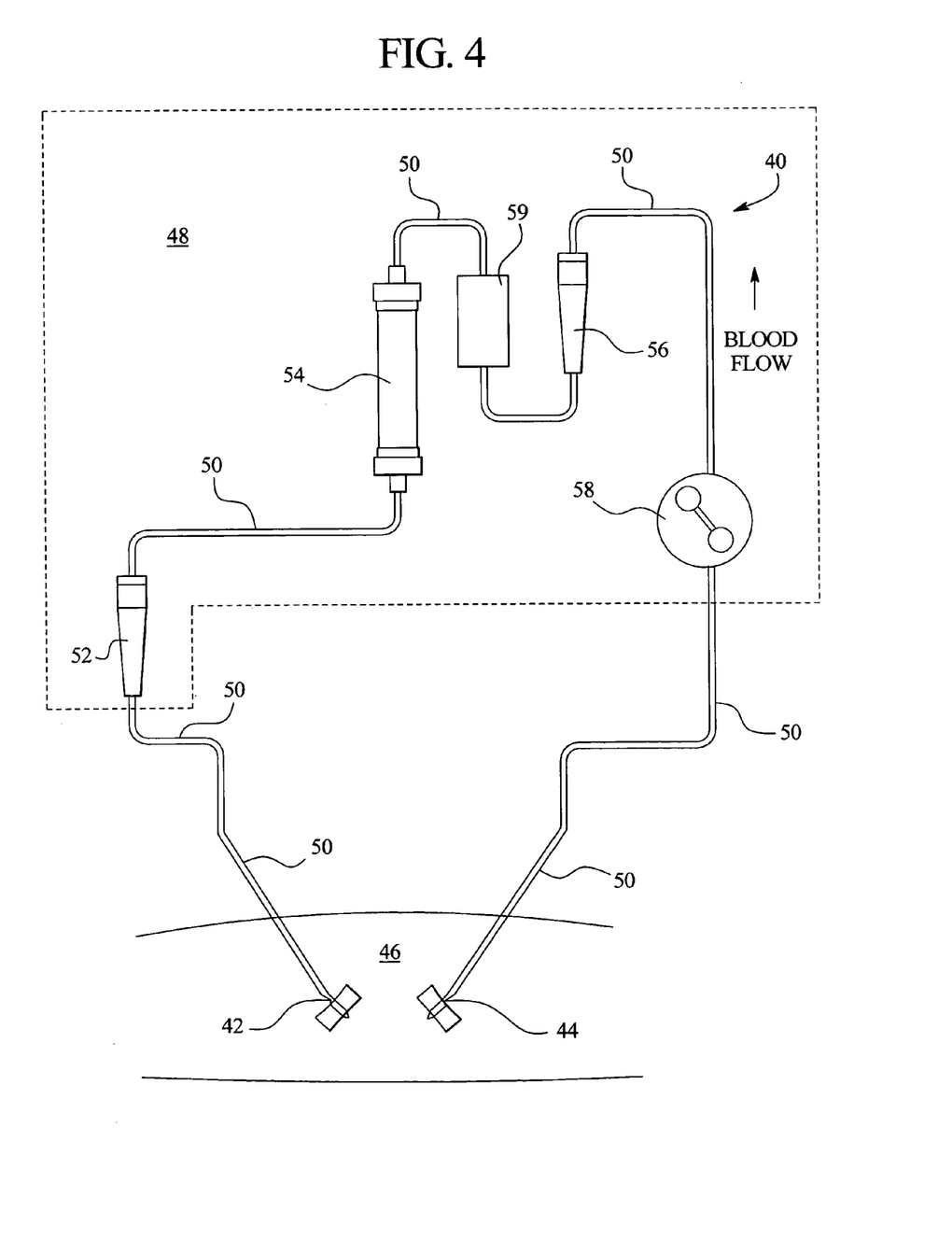
FIG. 4 schematically illustrates a dialysis system pursuant to an embodiment of the present invention.

As shown in FIG. 4, an embodiment of the present invention is illustrated as applied during dialysis therapy. In an embodiment, an apparatus 40 for dialysis includes a venous needle 42 and an arterial needle 44 inserted within a patient access 46. The venous needle and arterial needle are connected to a number of tube members 50 that can connect the various components of the apparatus 40 and the dialysis system 48 thereof including, for example, a venous drip chamber 52, a dialyzer 54, an arterial drip chamber 56, a blood pump 58, a cartridge 59 for removing uremic toxins, excess nitric oxide and/or the like, other suitable dialysis components and combinations thereof. It should be appreciated that one or more of the components of the dialysis system can be provided within a dialysis machine coupled to the blood circuit.

Figure 5:
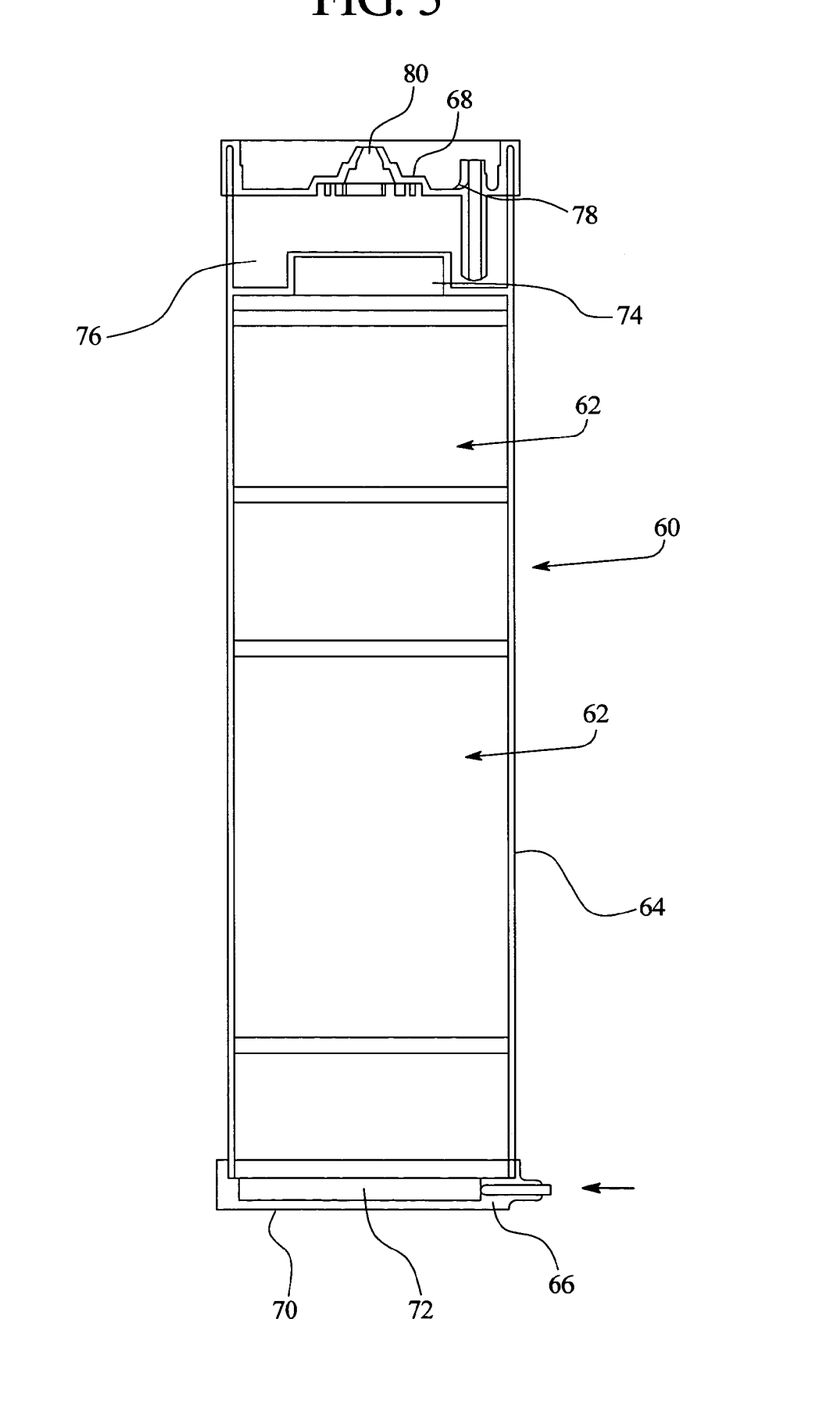
FIG. 5 schematically illustrates a cartridge according to an embodiment of the present invention.

Referring now to FIG. 5, a cross-sectional view of an embodiment of a cartridge 60 of the present invention is illustrated. The cartridge 60 includes a bed 62 of material that is designed to modify the chemistry of the dialysate and remove uremic toxins, excess nitric oxide and/or the like. At the same time, pursuant to an embodiment of the present invention, the cartridge 60 maintains electrolyte concentrations and the solution pH of the dialysate at physiologic levels.

The cartridge 60 generally includes a main body 64, an inlet cap 66, the bed 62, and an outlet cap 68. In the embodiment illustrated, fluid is routed into the cartridge 60 through the inlet cap 66 that is located at a bottom 70 of the cartridge 60. In the embodiment illustrated, a small open header chamber 72 prior to the bed 62 is used to distribute the flow of fluid evenly across the cross-section of the cartridge 60 and thereby the bed 62. The fluid preferably flows upwardly through the bed 62.

In the embodiment illustrated, downstream of the final section of the bed 62 there is located another open header chamber 74. The second open header chamber 74 is located before a gas separation chamber 76. The second header chamber 74 is used to maintain an even fluid velocity distribution throughout the resin bed 62.

The liquid level in the gas separation chamber 76 is maintained within a specified range to provide an air space above the liquid in the cartridge 60. Gases that are produced during therapy, e.g., carbon dioxide, are vented from the cartridge 60 to the environment through a passage 78 on the outlet cap 68. If desired, this passage 78 may include a filter member. A submerged, or partially submerged, barrier in the gas separation chamber 76 produces a flow pattern that restricts gases from being drawn to the liquid outlet.

At the outlet cap 68 of the cartridge 60 the liquid outlet port 80 is located. The liquid outlet 80 port removes liquid from the chamber of the cartridge 60 through the outlet cap 68 using a siphon action. If desired, an additional port may be used to add a chemical concentrate to the volume of liquid in the gas separation chamber to reconstitute the chemical composition of the fluid outflow.

In an embodiment, the interior of the cartridge 60 has a rough surface. The rough surface is designed so that it prevents fluid from flowing along the sides of the exterior by passing the resin bed 62.

The bed 62 material functions to remove waste, toxins and/or the like including excess nitric oxide from a solution used during dialysis as previously discussed. The bed of material includes the therapeutic compositions of the present invention, such as the nitronyl nitroxide monoradical, the flavonoid derivatives, the vitamin B12 derivatives, the like and combinations thereof. The therapeutic compositions can be contained in the bed in any suitable manner. For example, the therapeutic compositions can be attached to a material that acts as a support thereof. The material can include any suitable types of materials of any suitable particle size, such as resin material, bead material, and any other suitable types of material including inorganic and organic types. Alternatively, the therapeutic composition can be mixed with the material in any suitable manner. Additional other layers can include a urease layer, a layer of zirconium phosphate, a layer of zirconium oxide, a layer of carbon and the like. In an embodiment, the cartridge can include one or more layers composed of a membrane. The membrane can be made of any suitable material and have a modified surface such that a ligand can attach thereto. The ligand can include the therapeutic compositions of the present invention as previously discussed. An example of a cartridge can be found in U.S. patent Ser. No. 09/990,673, entitled METHOD AND COMPOSITION FOR REMOVING UREMIC TOXINS IN DIALYSIS PROCESS, filed on Nov. 13, 2001, the disclosure of which is herein incorporated by reference.

Figure 6:
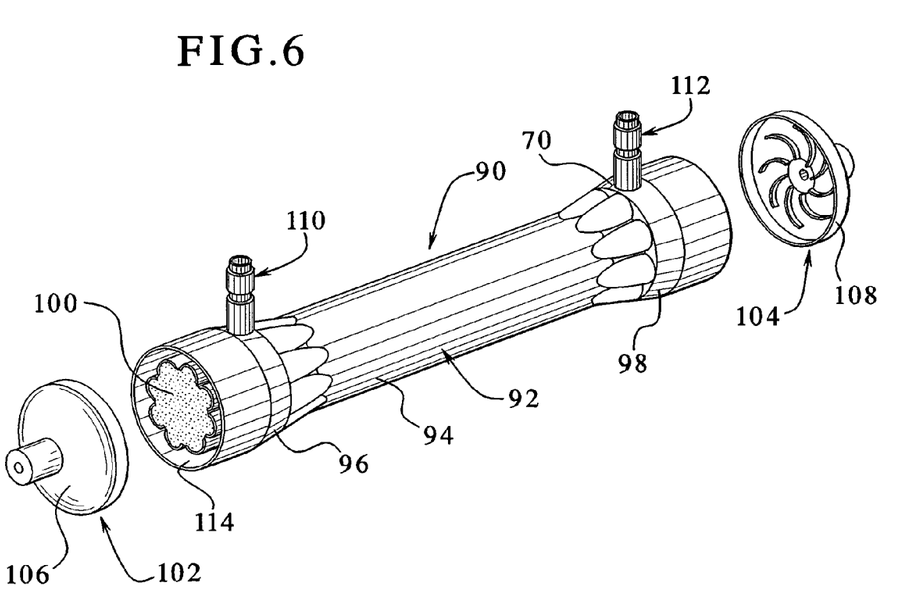
FIG. 6 schematically illustrates a dialyzer pursuant to an embodiment of the present invention.

Referring to FIG. 6, a dialyzer 90 is generally illustrated. The dialyzer 90 includes a body member 92 that generally includes a casing. The casing includes a core section 94 as well as two bell members 96 and 98 located at each end of the dialyzer 90. Located within the core or casing is a fiber bundle 100.

The fiber bundle 100 includes a plurality of hollow fiber membranes. The membranes are semi-permeable having a selective permeability. The membranes are bundled together and assembled in the casing in a manner allowing blood to flow simultaneously in a parallel manner through the lumina of the fibers while a blood cleansing liquid (dialysate) is simultaneously passed through the casing. In theory, this allows the dialysate to bathe the exterior surface of the hollow fibers. A variety of compounds can be used to produce selective permeable membranes including polymers such as, cellulose; cellulose acetate; polyamide; polyacrylonitarile; polyvinyl alcohol; polymethacrylate; polysulfone; polyolefin and/or the like. The fiber bundle 100 is encapsulated at each end of the dialyzer to prevent blood flow around the fibers.

Located at a first end of the dialyzer is a fluid inlet 102 and at a second end a fluid outlet 104 defined by a fluid inlet header 106 and a fluid outlet header 108. The dialyzer 90 also includes a dialysate inlet 110 and a dialysate outlet 112. In the preferred embodiment illustrated, the dialysate inlet 110 and dialysate outlet 112 define fluid flow channels that are in a radial direction, i.e., perpendicular to the fluid flow path of the blood. The dialysate inlet 110 and dialysate outlet 112 are designed to allow dialysate to flow into an interior 114 of the dialyzer bathing the exterior surfaces of the fibers and the fiber bundle 100 and then out through the outlet 112. This, as is known in the art, causes waste and other toxins to be removed from the blood through the semipermeable membrane of the fibers and carried away by the dialysate.

As previously discussed, the semipermeable membranes of the dialyzer can have a modified surface such that one or more ligands are attached thereto. The ligands include the therapeutic compositions, such as flavonoid derivatives, vitamin B12 derivatives, and/or the like. This allows the semipermeable membranes to remove an effective amount of excess nitric oxide from fluid undergoing dialysis and in contact with the membranes.

A variety of different header and dialyzer designs can be utilized. For example, U.S. Pat. No. 6,623,638 and U.S. Patent Publication No. 2003/0075498 provide a number of different examples illustrative of the present invention. The disclosures of U.S. Pat. No. 6,623,638 and U.S. Patent Publication No. 2003/0075498 are herein incorporated by reference.

In an embodiment, the therapeutic compositions of the present invention are added to dialysis solutions, such as hemodialysis solutions, peritoneal dialysis solutions and the like. The therapeutic compositions can be added to the dialysis solutions in any suitable and effective amount such that the compositions can effectively act to remove excess nitric oxide during dialysis therapy. This can prevent and/or treat disease, such as intradialytic hypotension and the like, associated with kidney disease patients.

In general, the dialysis solution includes an osmotic agent, such as dextrose, glycerol, glucose polymers including icodextrin, polyglucose, polypeptides, amino acids and/or other suitable constituents in any suitable amount. The dialysis solution further includes one or more electrolytes, such as sodium, calcium, potassium, magnesium, chloride and/or the like in any suitable amount. The dialysis solution may also include other constituents, such as buffers including lactate, bicarbonate, and/or the like, and other constituents, such as stabilizers.

It should be appreciated that the components of the dialysis solutions of the present invention can be housed or contained in any suitable manner such that the dialysis solutions can be effectively prepared and administered. In an embodiment, the present invention includes a multi-part dialysis solution in which two or more parts are formulated and stored separately, and then mixed just prior to use. A variety of containers can be used to house the various parts of the dialysis solution, such as separate containers (i.e., flasks, bags and the like) that are connected by a suitable fluid communication mechanism. An example of a multi-chamber container is set forth in U.S. Pat. No. 5,431,496, the disclosure of which is herein incorporated by reference. Another example of a multi-chamber container is set forth in U.S. Pat. No. 4,396,383, the disclosure of which is herein incorporated by reference. An example of a multi-chamber solution bag that includes a peel seal is disclosed in U.S. Pat. No. 6,319,243, the disclosure of which is herein incorporated by reference. Examples of peelable seals and containers using same can be found in U.S. Pat. No. 6,663,743 issued on Dec. 16, 2003, divisional of U.S. patent application Ser. No. 08/033,233 filed on Mar. 16, 1993 entitled "PEELABLE SEAL AND CONTAINER HAVING SAME", the disclosures of which are herein incorporated by reference.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of providing dialysis to a patient, the method comprising:
   providing a dialysis solution including an osmotic agent and a pharmaceutically active agent comprising a nitronyl nitroxide monoradical selected from the group consisting of 1,3-dihydroxy-2-(2,4-dihydroxyphenyl)-4,4,5,5-tetramethylimidazolidine; 1,3-dihydroxy-2-(3,4-dihydroxyphenyl)-4,4,5,5-tetramethylimidazolidine; 1,3-dihydroxy-2-(4-pyridyl)-4,4,5,5-tetramethylimidazolidine; 1,3-dihydroxy-2-(2-thienyl)-4,4,5,5-tetramethylimidazolidine; 1,3-Dihydroxy-2-(2-furyl)-4,4,5,5-tetramethylimidazolidine; and combinations thereof;
   providing the dialysis solution to the patient; and
   removing an excess amount of nitric oxide from the patient effectively without inhibiting synthesis of nitric oxide.

2. The method of claim 1 wherein the composition is administered intravenously to the patient.

3. A method of preventing or treating intradialytic hypotension in a patient undergoing dialysis, the method comprising the steps of:
   providing a composition to the patient wherein the composition includes a pharmaceutically active agent that includes a nitric oxide scavenger composition; and
   removing an excess amount of nitric oxide from the patient effectively without inhibiting synthesis of nitric oxide.

4. The method of claim 3 wherein the nitric oxide scavenger composition is selected from the group consisting of a nitronyl nitroxide monoradical, a B12 derivative, a flavonoid derivative and combinations thereof.

5. The method of claim 4 wherein the nitric oxide scavenger composition is selected from the group consisting of:
   1,3-dihydroxy-2-(2,4-dihydroxyphenyl)-4,4,5,5-tetramethylimidazolidine;
   1,3-dihydroxy-2-(3,4-dihydroxyphenyl)-4,4,5,5-tetramethylimidazolidine;
   1,3-dihydroxy-2-(4-pyridyl)-4,4,5,5-tetramethylimidazolidine;
   1,3-dihydroxy-2-(2-thienyl)-4,4,5,5-tetramethylimidazolidine; 1,3-Dihydroxy-2-(2-furyl)-4,4,5,5-tetramethylimidazolidine;
   hydroxocobalamin; cyanocobalamin; pelargonidin; cyanidin; delphinidin and combinations thereof.

6. The method of claim 3 wherein the composition is administered intravenously to the patient.

7. The method of claim 3 wherein the composition is orally administered to the patient.

8. The method of claim 3 wherein the composition is attached to a semipermeable membrane material within a dialyzer allowing removal of the excess nitric oxide during dialysis.

9. The method of claim 8 wherein the composition is attached to a bead material within a cartridge further allowing removal of the excess nitric oxide during dialysis.

10. A method of providing dialysis to a patient, the method comprising:
    providing a dialysis solution including an osmotic agent and a pharmaceutically active agent comprising a B12 derivative selected from the group consisting of hydroxocobalamin, cyanocobalamin and combinations thereof;
    providing the dialysis solution to the patient; and
    removing an excess amount of nitric oxide from the patient effectively without inhibiting synthesis of nitric oxide.

11. A method of providing dialysis to a patient, the method comprising:
    providing a composition including a pharmaceutically active agent comprising a flavonoid derivative selected from the group consisting of pelargonidin, cyanidin, delphinidin and combinations thereof;
    providing the composition to the patient; and
    removing an excess amount of nitric oxide from the patient effectively without inhibiting synthesis of nitric oxide.

12. A method of providing dialysis to a patient, the method comprising:
    attaching a pharmaceutically active agent to a semipermeable membrane within a dialyzer, the pharmaceutically active agent comprising at least one of i) a nitronyl nitroxide monoradical selected from the group consisting of 1,3-dihydroxy-2-(2,4-dihydroxyphenyl)-4,4,5,5-tetramethylimidazolidine; 1,3-dihydroxy-2-(3,4-dihydroxyphenyl)-4,4,5,5-tetramethylimidazolidine; 1,3-dihydroxy-2-(4-pyridyl)-4,4,5,5-tetramethylimidazolidine; 1,3-dihydroxy-2-(2-thienyl)-4,4,5,5-tetramethylimidazolidine; 1,3-Dihydroxy-2-(2-furyl)-4,4,5,5-tetramethylimidazolidine; and combinations thereof, and ii) a B12 derivative selected from the group consisting of hydroxocobalamin, cyanocobalamin and combinations thereof;
    passing a dialysis fluid through the dialyzer to remove excess nitric oxide from the dialysis fluid; and
    providing the dialysis fluid to the patient during dialysis treatment.

13. A method of providing dialysis to a patient, the method comprising:
    attaching a pharmaceutically active agent to a bead material within a cartridge, the pharmaceutically active agent comprising at least one of i) a nitronyl nitroxide monoradical selected from the group consisting of 1,3-dihydroxy-2-(2,4-dihydroxyphenyl)-4,4,5,5-tetramethylimidazolidine; 1,3-dihydroxy-2-(3,4-dihydroxyphenyl)-4,4,5,5-tetramethylimidazolidine; 1,3-dihydroxy-2-(4-pyridyl)-4,4,5,5-tetramethylimidazolidine; 1,3-dihydroxy-2-(2-thienyl)-4,4,5,5-tetramethylimidazolidine; 1,3-Dihydroxy-2-(2-furyl)-4,4,5,5-tetramethylimidazolidine; and combinations thereof, and ii) a B12 derivative selected from the group consisting of hydroxocobalamin, cyanocobalamin and combinations thereof;
    passing a dialysis fluid through the cartridge to remove excess nitric oxide from the dialysis fluid; and
    providing the dialysis fluid to the patient during dialysis treatment.

* * * * *